(12) United States Patent
Adachi (10) Patent No.: US 12,350,100 B2
(45) Date of Patent: Jul. 8, 2025

(54) ULTRASONIC DEVICE AND CONTROL METHOD OF ULTRASONIC DEVICE

(71) Applicant: Socionext Inc., Kanagawa (JP)

(72) Inventor: Naoto Adachi, Yokohama (JP)

(73) Assignee: ABLIC INC., Nagano (JP)

( * ) Notice: Subject to any disclaimer, the term of this patent is extended or adjusted under 35 U.S.C. 154(b) by 156 days.

(21) Appl. No.: 18/310,231

(22) Filed: May 1, 2023

(65) Prior Publication Data

US 2023/0263503 A1    Aug. 24, 2023

Related U.S. Application Data

(63) Continuation of application No. PCT/JP2020/042628, filed on Nov. 16, 2020.

(51) Int. Cl.
 *A61B 8/00* (2006.01)
(52) U.S. Cl.
 CPC .............. *A61B 8/4483* (2013.01); *A61B 8/54* (2013.01); *A61B 8/52* (2013.01)
(58) Field of Classification Search
 CPC ............ A61B 8/4483; A61B 8/54; A61B 8/52
 See application file for complete search history.

(56) References Cited

U.S. PATENT DOCUMENTS

| | | | | |
|---|---|---|---|---|
| 5,873,830 A | * | 2/1999 | Hossack | G01S 7/52085 600/447 |
| 2004/0025592 A1 | * | 2/2004 | Thomas | B29C 45/76 73/579 |
| 2009/0150692 A1 | | 6/2009 | Poland | |
| 2009/0198138 A1 | | 8/2009 | Uchikawa et al. | |
| 2011/0213260 A1 | * | 9/2011 | Keel | A61B 5/7271 600/513 |

(Continued)

FOREIGN PATENT DOCUMENTS

| | | |
|---|---|---|
| JP | H04-092652 A | 3/1992 |
| JP | 2004-166745 A | 6/2004 |

(Continued)

OTHER PUBLICATIONS

International Search Report (ISR) dated Dec. 22, 2020 issued in International Patent Application No. PCT/JP2020/042628, with English translation.

*Primary Examiner* — Dixomara Vargas
(74) *Attorney, Agent, or Firm* — Rimon P.C.

(57) ABSTRACT

An ultrasonic device includes: a plurality of oscillation elements to generate ultrasonic waves toward a subject, and generate voltages according to ultrasonic waves reflected by the subject; a data generator to generate a predetermined number of sets of time-series data, each of the sets indicating change in time in a plurality of voltages generated by a predetermined number of oscillation elements, among the voltages generated by the plurality of oscillation elements; a data accumulator to accumulate the sets of time-series data generated by the data generator; a selector to select time-series data from among those generated by the data generator or those accumulated in the data accumulator; a data processor to generate image data by processing a predetermined number of sets of the selected time-series data; and a controller to cause the data generator to stop generating time-series data while the selector selects the accumulated time-series data.

8 Claims, 8 Drawing Sheets

(56) References Cited

U.S. PATENT DOCUMENTS

| | | |
|---|---|---|
| 2018/0199821 A1 | 7/2018 | Hashimoto et al. |
| 2019/0201042 A1* | 7/2019 | Nott ........................ A61B 34/76 |
| 2023/0270419 A1* | 8/2023 | Adachi ................. G01S 7/5208 |
| | | 600/437 |
| 2024/0390002 A1* | 11/2024 | Creamer ................ G16H 40/63 |

FOREIGN PATENT DOCUMENTS

| | | |
|---|---|---|
| JP | 2005-323894 A | 11/2005 |
| JP | 2008-520314 A | 6/2008 |
| JP | 2013-090839 A | 5/2013 |
| WO | 2005/065547 A1 | 7/2005 |
| WO | 2017/056463 A1 | 4/2017 |

* cited by examiner

ULTRASONIC DEVICE AND CONTROL METHOD OF ULTRASONIC DEVICE

CROSS-REFERENCE TO RELATED APPLICATIONS

This U.S. non-provisional application is a continuation application of and claims the benefit of priority under 35 U.S.C. § 365(c) from PCT International Application PCT/JP2020/042628 filed on Nov. 16, 2020, which is designated the U.S., the entire contents of which are incorporated herein by reference.

TECHNICAL FIELD

The present disclosure relates to an ultrasonic device and a method of controlling an ultrasonic device.

BACKGROUND ART

Ultrasonic devices that generate ultrasonic waves toward a living body and generate ultrasonic image data from ultrasonic waves reflected by the living body have been known. This type of ultrasonic device improves the image quality of ultrasonic images by, for example, generating multiple reception beams for respective transmission beams transmitted to the living body from multiple oscillation elements.

RELATED ART DOCUMENTS

Patent Documents

[Patent Document 1] Japanese Laid-Open Patent Application No. 2005-323894
[Patent Document 2] WO 2005/065547
[Patent Document 3] Japanese Laid-Open Patent Application No. 2004-166745

Recently, ultrasonic devices have become smaller and wireless; for example, ultrasonic probes that have built-in basic processing functions to generate ultrasonic images have been developed. In such ultrasonic devices, increasing the number of reception channels, which is the number of reception signals of ultrasonic waves (the number of oscillation elements) used for generating ultrasonic image data, results in higher quality of ultrasonic images, but consumes more power. Therefore, for example, mobile ultrasonic devices in which low power consumption is required to be driven by a battery, have fewer reception channels and lower ultrasonic image quality as compared to stationary ultrasonic devices.

SUMMARY

According to one aspect in the present disclosure, an ultrasonic device includes: a plurality of oscillation elements configured to generate ultrasonic waves toward a subject, and generate voltages according to ultrasonic waves reflected by the subject; a data generator configured to generate a predetermined number of sets of time-series data, each of the sets indicating change in time in a plurality of voltages generated by a predetermined number of oscillation elements, among the voltages generated by the plurality of oscillation elements; a data accumulator configured to accumulate the sets of time-series data generated by the data generator; a selector configured to select time-series data from among those generated by the data generator or time-series data from among those accumulated in the data accumulator; a data processor configured to generate image data by processing a predetermined number of sets of time-series data selected by the selector; and a controller configured to cause the data generator to stop generating time-series data while the selector selects the time-series data accumulated in the data accumulator.

EMBODIMENTS FOR CARRYING OUT THE INVENTION

In the following, embodiments will be described with reference to the drawings. According to the disclosed techniques, the power consumption of the ultrasonic device can be reduced without degrading the image quality of an ultrasonic image.

In the following, for a signal line through which information such as a signal is transmitted, the same reference numeral as the signal name will be used. A single signal line illustrated in the drawings may be constituted with multiple bits.

First Embodiment

Figure 1:
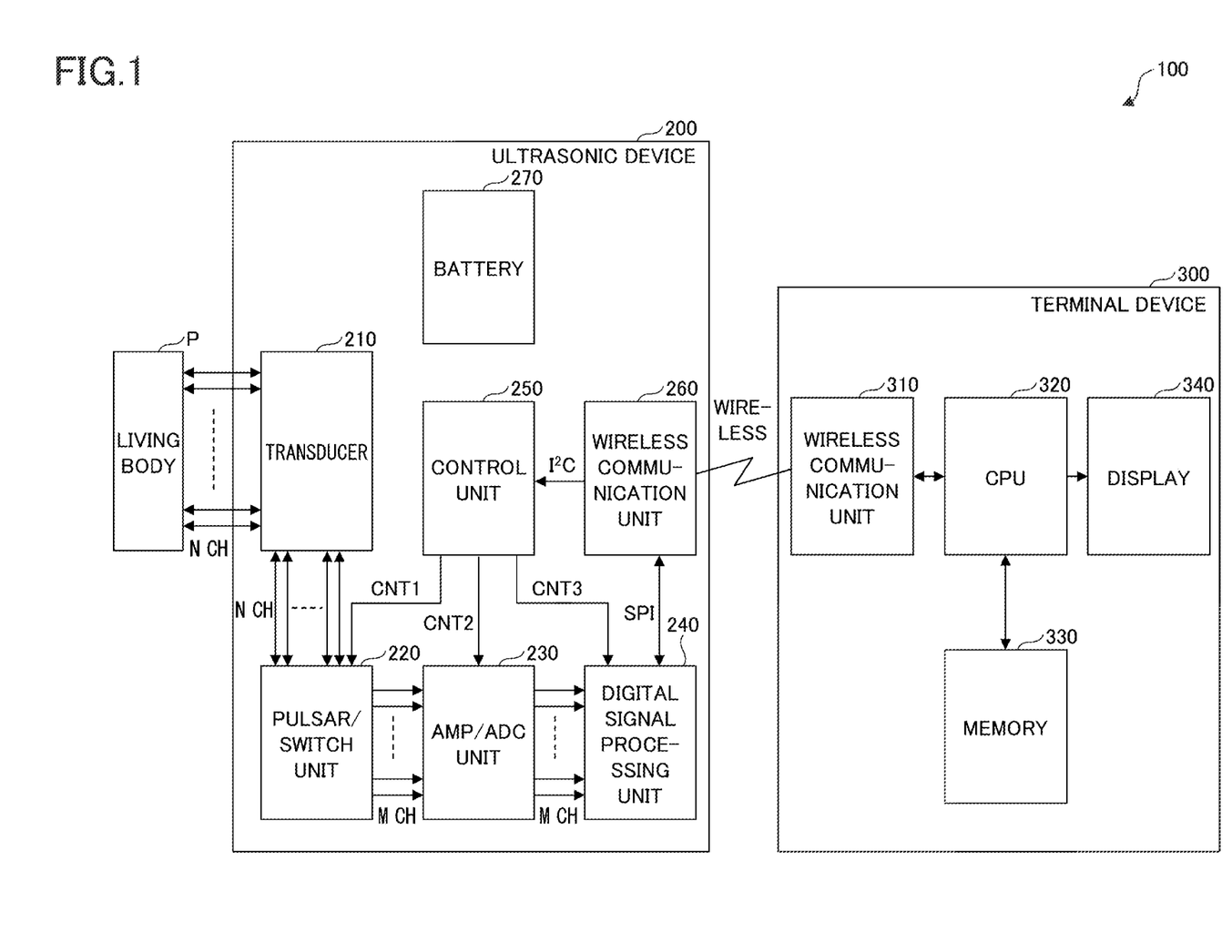
FIG. 1 is a block diagram illustrating an example of an ultrasonic diagnostic system including an ultrasonic device in a first embodiment.

FIG. 1 illustrates an example of an ultrasonic diagnostic system 100 including an ultrasonic device 200 in a first embodiment. The ultrasonic diagnostic system 100 includes an ultrasonic device 200 and a terminal device 300. The ultrasonic device 200 and the terminal device 300 execute wireless communication with each other. For example, the terminal device 300 is a portable general-purpose terminal such as a tablet terminal or a smartphone, or a general-purpose terminal such as a personal computer.

The ultrasonic device 200 is integrated with, for example, an ultrasonic probe and, and housed inside the housing of the ultrasonic probe. The ultrasonic device 200 includes a transducer 210, a pulsar/switch unit 220, an AMP (Amplifier)/ADC (Analog to Digital Converter) unit 230, a digital signal processing unit 240, a control unit 250, a wireless communication unit 260, and a battery 270. The terminal device 300 includes a wireless communication unit 310, a CPU (Central Processing Unit) 320, a memory 330, and a display 340.

The ultrasonic device 200 generates ultrasonic waves toward a living body P (subject), receives reflected waves (ultrasonic waves) reflected by the living body P, and generates ultrasonic image data based on the received reflected waves. The ultrasonic device 200 transmits the generated ultrasonic image data wirelessly to the terminal device 300. The terminal device 300 displays the ultrasonic image data received from the ultrasonic device 200 on the display 340 as an ultrasonic image.

The transducer 210 includes an oscillation element array in which multiple oscillation elements (not illustrated) are arranged in an array at positions opposite to a measurement region of an ultrasonic image in the living body P (subject). The transducer 210 outputs ultrasonic waves generated by a predetermined number of the oscillation elements in the oscillation element array toward the living body P, based on pulse signals generated by the pulsar/switch unit 220. In this embodiment, the oscillation element array includes N oscillation elements, and outputs M channels (M ch) of ultrasonic waves among N channels (N ch) to the living body.

Ultrasonic waves entering the living body P are reflected at a boundary at which the acoustic impedance becomes different. The transducer 210 receives ultrasonic waves (reflected waves) reflected from the living body P with N oscillation elements. The N oscillation elements convert the received ultrasonic waves into voltages, and output these to the pulsar/switch unit 220 as voltage signals of N channels. The transducer 210 and the pulsar/switch unit 220 are interconnected by signal lines of N channels.

The pulsar/switch unit 220 includes a pulsar and a switch, and operates based on a control signal CNT1 output from the control unit 250. In the case where the transducer 210 transmits ultrasonic waves to the living body P, the pulsar/switch unit 220 transmits M pulse signals generated by the pulsar to the M oscillation elements of the transducer 210 via a switch at a predetermined timing. Although not limited in particular, for example, 'N' is 128 and 'M' is 32. 'N' may be 196 or 256, and 'M' may be 16 or 64.

In addition, in the case where the transducer 210 receives ultrasonic waves from the living body P, the pulsar/switch unit 220 selects, via the switch, voltage signals of M channels from among the voltage signals of N channels output from the transducer 210. The M channels selected by the pulsar/switch unit 220 is the same as the M channels from which the pulse signal was output. Then, the pulsar/switch unit 220 outputs the voltage signals of the selected M channels to the AMP/ADC unit 230.

The AMP/ADC unit 230 operates based on a control signal CNT2 output from the control unit 250. The AMP/ADC unit 230 includes M AMP (not illustrated, also referred to as AMP), and M analog-to-digital converters (also referred to as ADC). Each of the AMP amplifies a voltage signal indicating a reflected wave of an ultrasonic wave in a corresponding one of the M channels received from the pulsar/switch unit 220, and outputs an amplified voltage signal to a corresponding one of the ADC. The number of channels of the voltage signals received by the AMP/ADC unit 230 from the pulsar/switch unit 220 is also referred to as the number of reception channels.

Each of the ADC sequentially converts a voltage signal (analog signal) amplified by a corresponding one of the AMP into digital data, to output digital data of M channels to the digital signal processing unit 240. Here, the M ADC generate respective digital data in time series, indicating change in time in the voltages generated by the M oscillation elements based on the reflected waves. In the following, the digital data in time series is also referred to as time-series data.

The digital signal processing unit 240 operates based on a control signal CNT3 output from the control unit 250. The digital signal processing unit 240 applies various processing to the time-series data of M channels received from the AMP/ADC unit 230, to generate image data representing an ultrasonic image, and outputs the generated image data to the wireless communication unit 260. For example, the digital signal processing unit 240 and the wireless communication unit 260 are mutually connected via a SPI (Serial Peripheral Interface) bus.

For example, by using the time-series data of M channels received from the pulsar/switch unit 220, the digital signal processing unit 240 executes a process of adjusting the amount of delay of each voltage signal in the M channels corresponding to reflected waves from the living body P; a process of averaging (phased addition); a gain correction process that takes attenuation of reflected waves in the living body P into account; an envelope process to retrieve brightness information; or the like. Examples of the configuration and operations of the digital signal processing unit 240 will be described with FIG. 2 and thereafter.

The wireless communication unit 260 executes wireless communication with the wireless communication unit 310 of the terminal device 300 via, for example, a wireless network such as Wi-Fi (registered trademark, wireless LAN (Local Area Network)). Note that wireless communication between the wireless communication units 260 and 310 is not limited to Wi-Fi, and may be executed using a wireless network compliant with the other wireless standards. The wireless communication unit 260 outputs to the control unit 250, for example, a command to emit ultrasonic waves received from the terminal device 300, using an I2C (Inter-Integrated Circuit) interface bus. In addition, the wireless communication unit 260 transmits image data received from the digital signal processing unit 240 to the wireless communication unit 310 of the terminal device 300. The image data representing the ultrasonic image transmitted from the ultrasonic device 200 to the terminal device 300 is digital data.

The control unit 250 controls the entirety of the ultrasonic device 200. For example, the control unit 250 is implemented by a control program executed by a processor such as a CPU that controls operations of the ultrasonic device 200. In this case, the control unit 250 may be included in a processor (not illustrated) installed in the ultrasonic device 200.

Note that the control unit 250 may be implemented by hardware such as a field-programmable gate array (FPGA) or an application specific integrated circuit (ASIC). In this case, the FPGA or ASIC may include an AMP/ADC unit 230 and a digital signal processing unit 240. Note that the control unit 250 may be implemented by interoperation of hardware and software.

For example, in response to receiving a command to start measurement from the terminal device 300 via the wireless communication unit 260, the control unit 250 controls the pulsar/switch unit 220 to cause the transducer 210 to output ultrasonic waves. The control unit 250 causes the digital signal processing unit 240 to generate image data for causing the display 340 to display reflected waves from the living body P as an ultrasonic image.

In addition, in response to receiving a command to stop measurement from the terminal device 300 via the wireless communication unit 260, the control unit 250 stops operations of the pulsar/switch unit 220, the digital signal processing unit 240, and the like. Note that the command to start measurement and the command to stop measurement may be executed based on an operation performed with an operation button, an operation switch, or the like (not illustrated) provided on the ultrasonic device 200.

The battery 270 can be charged via, for example, charging terminals (not illustrated) provided on the ultrasonic device 200. The battery 270 supplies power to the pulsar/switch unit 220, the AMP/ADC unit 230, the digital signal processing unit 240, the control unit 250, and the wireless communication unit 260 in the ultrasonic device 200. Note that the battery 270 may be charged without contact. In addition, the ultrasonic device 200 may be operated using an external power supply such as a commercial power supply, and in this case, the ultrasonic device 200 may or may not have the battery 270.

The wireless communication unit 310 of the terminal device 300 receives ultrasonic image data and the like, from the wireless communication unit 260 of the ultrasonic device 200. In addition, the wireless communication unit 310 transmits a command to emit ultrasonic waves or the like to the wireless communication unit 260 of the ultrasonic device 200. The CPU 320 controls the overall operations of the terminal device 300 by, for example, executing a program.

The memory 330 holds image data received by the wireless communication unit 310, various programs executed by the CPU 320, data used in various programs, and the like. The memory 330 may be an SRAM (Static Random Access Memory), a DRAM (Dynamic Random Access Memory), or a flash memory. Note that the memory 330 may include at least one of an SRAM, a DRAM, and a flash memory; and a storage device.

The display 340 displays image data received from the ultrasonic device 200 as an ultrasonic image. Here, the ultrasonic image displayed on the display 340 includes a moving image obtained while scanning the living body P by the ultrasonic device 200, and a still image obtained when the scanning of the living body P by the ultrasonic device 200 is stopped. In the case where the terminal device 300 is a portable terminal such as a tablet terminal, the display 340 may include a touch panel. Note that a wired communication unit may be provided in each of the ultrasonic device 200 and the terminal device 300 separately from the wireless communication units 260 and 310, to transmit and receive image data and the like via wire. The respective wired communication units may be provided in place of the wireless communication units 260 and 310.

Figure 2:
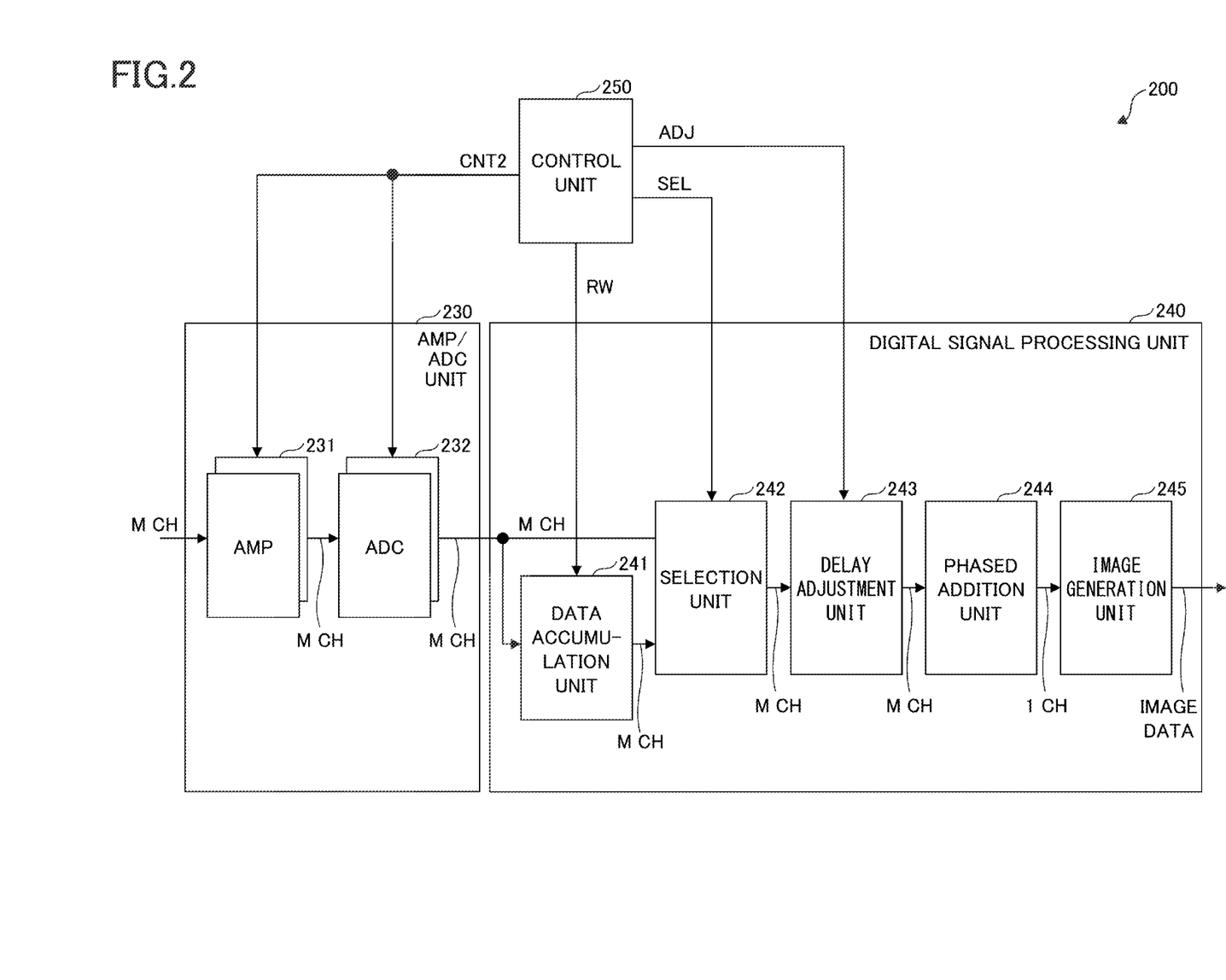
FIG. 2 is a block diagram illustrating an example of an AMP/ADC unit and a digital signal processing unit in FIG. 1.

FIG. 2 illustrates an example of the AMP/ADC unit 230 and the digital signal processing unit 240 in FIG. 1. The AMP/ADC unit 230 includes the M AMP 231 operating simultaneously and the M ADC 232 operating simultaneously. The digital signal processing unit 240 includes a data accumulation unit 241, a selection unit 242, a delay adjustment unit 243, a phased addition unit 244, and an image generation unit 245.

As described above, each of the M AMP 231 amplifies a voltage signal indicating a reflected wave of an ultrasonic wave in a corresponding one of the M channels received from the pulsar/switch unit 220, and outputs an amplified voltage signal to a corresponding one of the ADC 232. Each of the M ADC 232 converts a voltage signal of a corresponding one of the M channels received from the corresponding AMP 231 into time-series data, and output the time-series data obtained by the conversion, to the digital signal processing unit 240. The M ADC 232 are an example of a data generator that generates a predetermined number of sets of time-series data, each of the sets indicating change in time in a plurality of voltages generated by a predetermined number of oscillation elements.

While receiving a control signal CNT2 indicating a power-down command from the control unit 250, each of the AMP 231 and the ADC 232 stops operations to transition to a power-down state. For example, every time the switch of the pulsar/switch unit 220 selects predetermined signals of M channels from among the signals of N channels from the transducer 210, the control unit 250 operates the AMP 231 and the ADC 232 for a certain period of time, and then, stops the operations for a certain period of time.

The data accumulation unit 241 operates in response to a read/write signal RW from the control unit 250. For example, the read/write signal RW includes address information representing a write position or a read position of data in the data accumulation unit 241. The data accumulation unit 241 includes a register or memory capable of holding time-series data of M channels corresponding to reflected waves of ultrasonic waves for a predetermined time.

The data accumulation unit 241 accumulates (writes) the time-series data of M channels output from the M ADC 232. From among the accumulated time-series data of M channels, the data accumulation unit 241 reads data within a time range indicated from the control unit 250, and outputs the data to the selection unit 242.

The selection unit 242 operates based on a selection signal SEL from the control unit 250. During a period while the AMP/ADC unit 230 operates, the control unit 250 outputs to the selection unit 242 a selection signal SEL for causing the selection unit 242 to select time-series data of M channels output from the ADC 232.

During a period while operations of the AMP/ADC unit 230 is stopped (power-down period), the control unit 250 outputs to the selection unit 242 a selection signal SEL for causing the selection unit 242 to select time-series data of M channels output from the data accumulation unit 241. At this time, the control unit 250 causes the data accumulation unit 241 to output time-series data within a predetermined time range among time-series data accumulated in the data accumulation unit 241. The selection unit 242 outputs the selected time-series data of M channels to the delay adjustment unit 243.

The control unit 250 causes the ADC 232 to operate, for example, during a period corresponding to a time when the digital signal processing unit 240 can generate one line of image data. The digital signal processing unit 240 uses the time-series data of M channels output from the ADC 232 to generate one line of image data. Here, the one line of image data is data used for generating one line of an ultrasonic image directed from the surface of the living body P in the depth direction into the body at one of the multiple positions of a band-shaped measurement region on the surface of the living body P opposite to the oscillation element array. In the following, a position of the measurement region at which one line of ultrasonic image is generated is also referred to as a transmission position.

During a period while the AMP/ADC unit 230 is powered down, the digital signal processing unit 240 uses the time-series data of M channels read from the data accumulation unit 241, to generate one line of image data in at least one of the other positions of the measurement region. The operation of the AMP/ADC unit 230 is stopped for a period during which the image data is generated using the time-series data read from the data accumulation unit 241. Therefore, compared with the case where the AMP/ADC unit 230 is operated all the time, the power consumption of the ultrasonic device 200 can be reduced. Image data of different transmission positions can be generated during a period while the AMP/ADC unit 230 is powered down; therefore, the power consumption of the ultrasonic device 200 can be reduced without degrading the image quality.

Further, the power consumption of the ultrasonic device 200 can be reduced, and thereby, the operable time of the battery 270 can be extended, and the operation time of the ultrasonic device 200 operating with the battery 270 can be extended. In addition, the power consumption of the ultrasonic device 200 can be reduced; therefore, the heat generation of the ultrasonic device 200 can be reduced, and the temperature rise of the ultrasonic device 200 can be suppressed. As a result, in the ultrasonic device 200 integrated with the ultrasonic probe, the operator gripping the ultrasonic probe and the subject (living body P) to which the ultrasonic probe is applied can be prevented from feeling uncomfortable with the temperature of the ultrasonic probe.

For example, in the case of using one set of time-series data of M channels from the ADC 232 for generating two lines of image data, the operation frequency of the AMP 231 and the ADC 232 is reduced to half. In the case of using one set of time-series data of M channels from the ADC 232 for generating four lines of image data, the operation frequency of the AMP 231 and the ADC 232 is reduced to ¼.

Most of the power of the ultrasonic device 200 under operation is consumed by the AMP/ADC unit 230. Therefore, in the case of generating two lines of image data from one set of time-series data of M channels, the power consumption of the ultrasonic device 200 can be reduced to almost half. In the case of generating four lines of image data from one set of time-series data of M channels, the power consumption of the ultrasonic device 200 can be reduced to almost ¼.

For example, in the case of causing the digital signal processing unit 240 to generate three lines of image data using time-series data from the data accumulation unit 241, the control unit 250 causes the data accumulation unit 241 to output three sets of time-series data of M channels whose time ranges differ from one another. Then, the digital signal processing unit 240 generates one line of image data corresponding to each of three adjacent positions in the measurement region.

The delay adjustment unit 243 operates based on control by the control unit 250. The delay adjustment unit 243 extracts data of a predetermined amount of delay for each channel from time-series data of M channels output from the selection unit 242, and outputs the extracted data of M channels to the phased addition unit 244. In other words, by extracting the data of the predetermined amount of delay from the time-series data of M channels, the delay adjustment unit 243 adjusts the amount of delay of the data indicating reflected waves of ultrasonic waves of M channels.

The control unit 250 outputs to the delay adjustment unit 243 different delay adjustment signals ADJ for the time-series data of M channels from the ADC 232 and for the time-series data of M channels from the data accumulation unit 241. Accordingly, the amount of delay of data for each channel extracted by the delay adjustment unit 243 differs between the time-series data of M channels from the ADC 232 and the time-series data of M channels from the data accumulation unit 241. Further, in the case of using the time-series data of M channels output multiple times from the data accumulation unit 241, for each set of time-series data to be used, the control unit 250 outputs to the delay adjustment unit 243 a delay adjustment signal ADJ that differentiates the amount of delay of the data for each channel extracted by the delay adjustment unit 243.

Respective amounts of delays of the data of M channels are determined by a relationship between the positions of the M oscillation elements that generate ultrasonic waves toward the living body P in the oscillation element array, and the positions that generate one line of image data in the measurement region of the living body P. Further, the respective amounts of delays of the data of M channels are determined according to the positions of image data generated on a line toward the interior of the body from the surface of the measurement region (transmission position) of the living body P.

The phased addition unit 244 sequentially adds the data of M channels whose amounts of delays are respectively adjusted by the delay adjustment unit 243 corresponding to one transmission position, and generates one line of data (1 ch) in the depth direction of the living body P at the transmission position. The phased addition unit 244 outputs the generated one line of data to the image generation unit 245.

Based on the data received from the phased addition unit 244, the image generation unit 245 generates image data of one line in the depth direction of the living body P at the transmission position, and outputs the generated image data to the wireless communication unit 260 in FIG. 1. Then, the one line of image data corresponding to the transmission position is transmitted to the terminal device 300, and displayed on the display 340 as an ultrasonic image. Note that the image generation unit 245 may execute signal processing such as a gain correction process or an envelope process, and then, generate image data.

Figure 3:
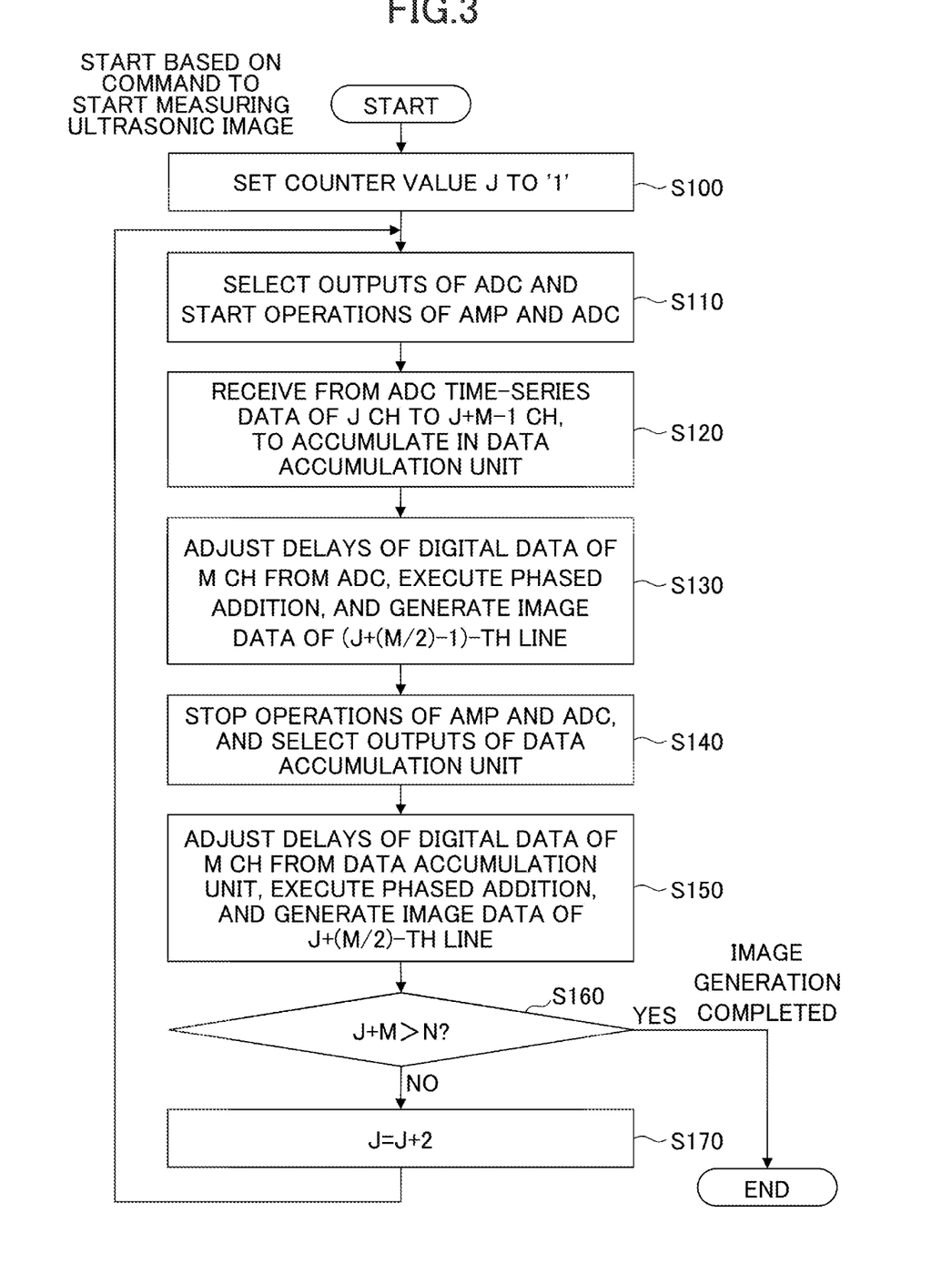
FIG. 3 is a flow chart illustrating an example of operations of the ultrasonic device in FIG. 1.

FIG. 3 illustrates an example of operations of the ultrasonic device 200 in FIG. 1. For example, an operation flow illustrated in FIG. 3 may be implemented by the control unit 250 (processor) executing a control program. In other words, FIG. 3 illustrates an example of a control method of the ultrasonic device 200 and a control program of the ultrasonic device 200. Note that in the following description, a channel (ch) may indicate a number (1, 2, 3, . . . , 128 counting from an oscillation element at one end) that identifies an oscillation element arranged in the oscillation element array. A line indicates a transmission position at which an ultrasonic image for one line of the measurement region of the living body P is generated.

For example, the operation flow illustrated in FIG. 3 is initiated in response to receiving a command to start measuring an ultrasonic image from the terminal device 300 in FIG. 1. Note that the number of channels N (e.g., 128 channels) of the transducer 210 and the number of channels M (e.g., 32 channels), which is the number of oscillation elements selected by the pulsar/switch unit 220, are determined when designing the ultrasonic device 200.

First, at Step S100, the control unit 250 sets the counter value J to '1'. The counter value J indicates the number assigned to a transmission position and the line number of one line of image data generated corresponding to the transmission position. Next, at Step S110, the control unit 250 causes the selection unit 242 to select outputs of the ADC 232, and causes the AMP 231 and the ADC 232 to start operations.

Next, at Step S120, the control unit 250 causes the pulsar/switch unit 220 to select voltage signals of M channels indicating reflected waves of the ultrasonic waves starting from a channel indicated by the counter value J to a channel J+M−1. The AMP 231 amplify the voltage signals of the M channels received from the pulsar/switch unit 220.

The ADC 232 convert the voltage signals amplified by the AMP 231 into time-series data. The digital signal processing unit 240 receives time-series data of M channels from J to J+M−1, which are output from the ADC 232, and accumulates the time-series data in the data accumulation unit 241.

Next, at Step S130, in order to generate image data of the (J+(M/2)−1)-th line, by using time-series data from the ADC 232 selected by the selection unit 242, the control unit 250 causes the delay adjustment unit 243 to adjust amounts of delays of the data of M channels. The delay adjustment unit 243 extracts data from the time-series data received from the ADC 232 at Step S120, to adjust the amounts of delays of the data.

The phased addition unit 244 executes phased addition of the data of M channels whose amounts of delays have been adjusted, to generate image data of the (J+(M/2)−1)-th line. Note that the line number of image data to be generated is not limited to J+(M/2)−1. The image data is transmitted to the terminal device 300 via the wireless communication unit 260, and displayed as an ultrasonic image on the display 340.

Next, at Step S140, the control unit 250 stops operations of the AMP 231 and the ADC 232, and causes the selection unit 242 to select outputs of the data accumulation unit 241.

Next, at Step S150, in order to generate image data of the J+(M/2)-th line, by using time-series data from the data accumulation unit 241 selected by the selection unit 242, the control unit 250 causes the delay adjustment unit 243 to adjust amounts of delays of the data of M channels. The delay adjustment unit 243 extracts data from the time-series data accumulated in the data accumulation unit 241 at Step S120, to adjust the amounts of delays of the data.

The phased addition unit 244 executes phased addition of the data of M channels whose amounts of delays have been adjusted, to generate image data of the J+(M/2)-th line. Note that the line number of image data to be generated by the phased addition unit 244 is not limited to J+(M/2). Based on the data received from the phased addition unit 244, the image generation unit 245 generates image data at the J+(M/2)-th line, and the generated image data is transmitted to the terminal device 300 via the wireless communication unit 260. Then, the image data is displayed on the display 340 as an ultrasonic image.

Next, at Step S160, the control unit 250 determines whether a value obtained by adding the number of channels M to the counter value J exceeds, for example, the number of channels N (the number of oscillation elements) of the transducer 210. If J+M exceeds the number of channels N, the control unit 250 completes the image generation operation as image data for all transmission positions has been generated in the measurement region. If J+M is less than or equal to the number of channels N, the control unit 250 transitions to the processing at Step S170 because there is a transmission position where image data has not been generated yet.

At Step S170, the control unit 250 increases the counter value J by '2', and then, the process returns to Step S110. Then, generation of the next two lines of image data is executed sequentially until J+M exceeds the number of channels N, and the ultrasonic image of the measurement region is displayed on the display 340.

The control unit 250 generates image data using the time-series data accumulated in the data accumulation unit 241, and then, the counter value J is increased by '2'. In addition, the range of oscillation elements selected by the switch is shifted by two. Accordingly, in the next processing loop, image data for the next transmission position after the transmission position at which the image data has been generated can be sequentially generated. As a result, an ultrasonic image with uninterrupted lines can be displayed on the display 340.

In this embodiment, in the case of generating image data for the J+(M/2)-th line, the digital signal processing unit 240 uses time-series data accumulated in the data accumulation unit 241. Accordingly, when generating image data for the J+(M/2)-th line, the control unit 250 can stop operations of the AMP 231 and the ADC 232.

Therefore, for approximately half the period of the operations to generate image data, the control unit 250 can stop operations of the AMP 231 and the ADC 232. As a result, compared with the case where the AMP 231 and the ADC 232 are operated all the time, the power consumption of the ultrasonic device 200 can be reduced to almost half. In other words, the power consumption of the ultrasonic device can be reduced without degrading the image quality of an ultrasonic image.

Figure 4:
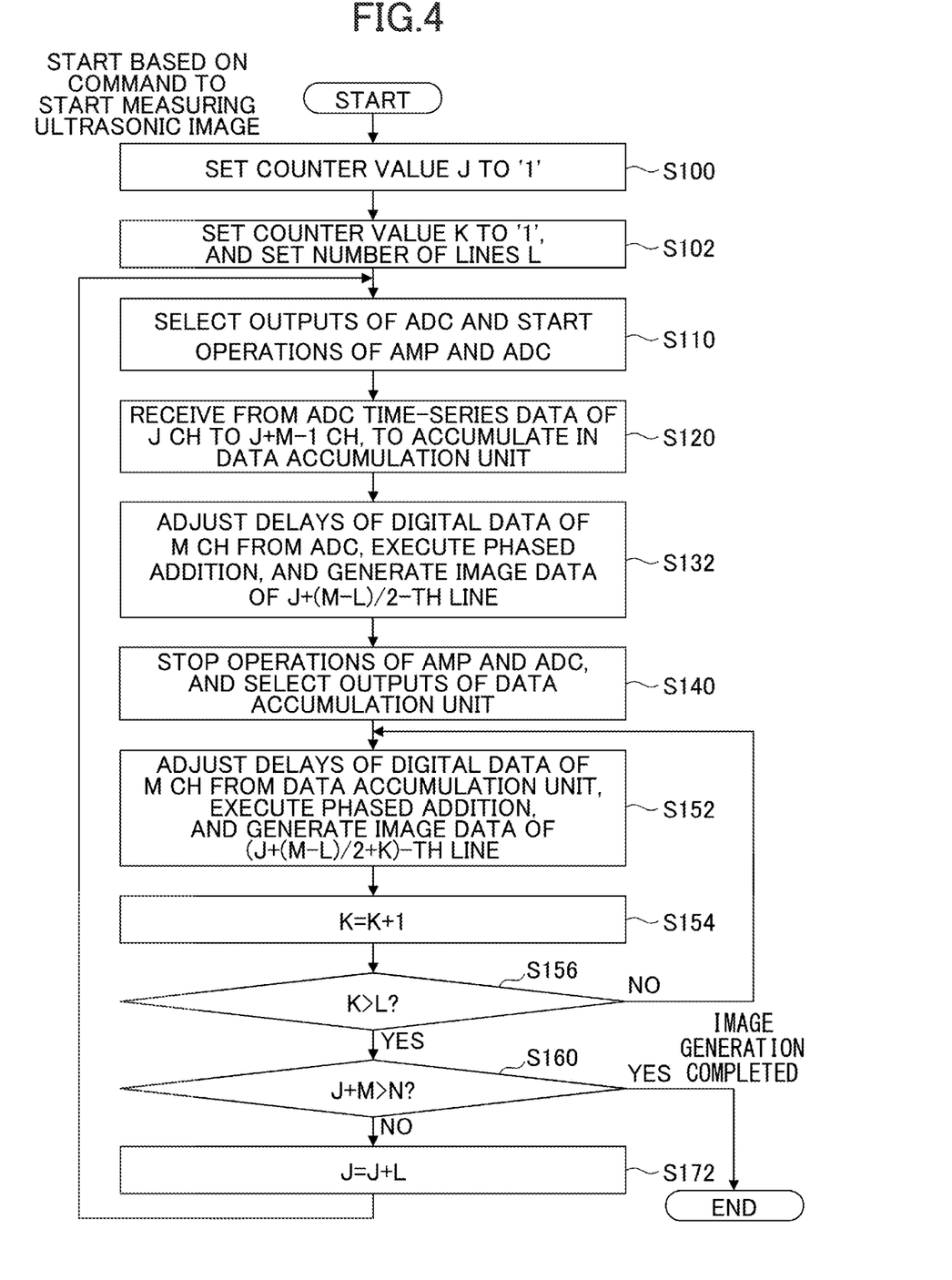
FIG. 4 is a flow chart illustrating another example of operations of the ultrasonic device in FIG. 1.

FIG. 4 illustrates another example of operations of the ultrasonic device 200 in FIG. 1. Operations that are substantially the same as those in FIG. 3 are assigned the same step numbers as in FIG. 3, and detailed description is omitted. An operation flow illustrated in FIG. 4 may also be implemented by the control unit 250 (processor) executing a control program. In other words, FIG. 4 illustrates an example of a control method of the ultrasonic device 200 and a control program of the ultrasonic device 200.

In FIG. 4, the ultrasonic device 200 can generate image data of any number L of lines using the time-series data of M channels generated in one conversion operation by the ADC 232. To that account, in FIG. 4, Step S102 is inserted between Steps S100 and S110 in FIG. 3. In addition, Step S132 is executed instead of Step S130 in FIG. 3, and Steps S152, S154, and S156 are executed instead of Step S150 in FIG. 3. Further, in FIG. 4, Step S172 is executed instead of Step S170 in FIG. 3.

At Step S102, the control unit 250 sets the counter value K to '1', and sets the number of lines L. For example, the number of lines L is the number of lines of image data generated using one set of time-series data output from the ADC 232. The counter value K indicates the number assigned to a line of image data to be generated among the L lines.

The operations at Steps S110 and S120 are the same as those in FIG. 3. Step S132 is substantially the same as Step S130 in FIG. 3 except that image data of the J+(M−L)/2-th line is generated. Step S152 is substantially the same as Step S150 in FIG. 3 except that image data of the (J+(M−L)/2+K)-th line is generated.

After Step S152, at Step S154, the control unit 250 increases the counter value K by '1'. Next, at Step S156, the control unit 250 determines whether the counter value K exceeds the number of lines L. If the counter value K exceeds the number of lines L, the control unit 250 determines that image data of all lines using the one set of time-series data output from the ADC 232 has been generated, and executes an operation at Step S160. If the counter value K is less than or equal to the number of lines L, the control unit 250 determines that there is a line for which image data has not been generated yet using the one set of time-series data output from the ADC 232, and returns the process to Step S152.

Then, at Step S160, the control unit 250 determines whether a value obtained by adding the number of channels M to the counter value J exceeds, for example, the number of channels N (the number of oscillation elements) of the transducer 210. If J+M is less than or equal to the number of channels N, the control unit 250 transitions to the processing at Step S172 because there is a transmission position where image data has not been generated yet.

At Step S172, the control unit 250 sets a new counter value J by adding the number of lines L to the counter value J, and returns to the processing at Step S110. Then, generation of the next L lines of image data is executed sequentially until J+M exceeds the number of channels N, and the ultrasonic image of the measurement region is displayed on the display 340.

By using the time-series data accumulated in the data accumulation unit 241, the control unit 250 generates image data of N−1 lines, and then, increases the counter value J by 'L'. In addition, the control unit 250 shifts the range of oscillation elements selected by the switch by L. Accordingly, in the next processing loop, image data for the next transmission position after the transmission position at which the image data has been generated can be sequentially generated. As a result, an ultrasonic image with uninterrupted lines can be displayed on the display 340.

In FIG. 4, the ultrasonic device 200 can generate image data of L lines using the one set of time-series data output from the ADC 232. Therefore, for approximately (L−1)/L of a period of the operations to generate an ultrasonic image, the control unit 250 can stop operations of the AMP 231 and the ADC 232. As a result, compared with the case where the AMP 231 and the ADC 232 are operated all the time, the power consumption of the ultrasonic device 200 can be reduced to almost 1/L. Note that operations in the case where the number of lines L is set to '2' is substantially the same as in FIG. 3.

As above, in this embodiment, multiple sets of image data of different transmission positions can be generated during the period while the AMP/ADC unit 230 is powered down; therefore, the power consumption of the ultrasonic device 200 can be reduced without degrading the image quality. By generating multiple sets of image data at different transmission positions during a period while the AMP/ADC unit 230 is powered down, the power consumption of the ultrasonic device 200 can be reduced further without degrading the image quality.

By wirelessly connecting the ultrasonic device 200 and the terminal device 300, the functions of the ultrasonic device 200 can be installed in the ultrasonic probe and integrated with the ultrasonic probe. Also in the case of driving the ultrasonic device 200 integrated with the ultrasonic probe by a battery, the power consumption of the ultrasonic device 200 can be reduced; therefore, the operable time of the battery 270 can be extended, and the operation time of the ultrasonic device 200 operating with the battery 270 can be extended.

In addition, the power consumption of the ultrasonic device 200 can be reduced; therefore, the heat generation of the ultrasonic device 200 can be reduced, and the temperature rise of the ultrasonic device 200 can be suppressed. The temperature rise of the ultrasonic device 200 can be suppressed regardless of use of a battery power supply or use of an external power supply. As a result, when using the ultrasonic device 200 integrated with the ultrasonic probe, the operator gripping the ultrasonic probe and the subject to which the ultrasonic probe is applied (living body P) can be prevented from feeling uncomfortable with the temperature of the ultrasonic probe.

For example, after generating image data of N−1 lines using time-series data accumulated in the data accumulation unit 241, the counter value J is increased by 'L'. In addition, the range of oscillation elements selected by the switch is shifted by N. Accordingly, in the next processing loop, image data for the next transmission position after the transmission position at which the image data has been generated can be sequentially generated. As a result, an ultrasonic image with uninterrupted lines can be displayed on the display 340.

Note that in the operation flow in FIG. 4, the ultrasonic device 200 may change the number of lines generated using time-series data accumulated in the data accumulation unit 241, according to the remaining capacity of the battery 270. For example, the ultrasonic device 200 may increase the number of lines L in FIG. 4 as the remaining capacity of the battery 270 decreases. Accordingly, the operable time of the battery 270 can be further lengthened.

Second Embodiment

Figure 5:
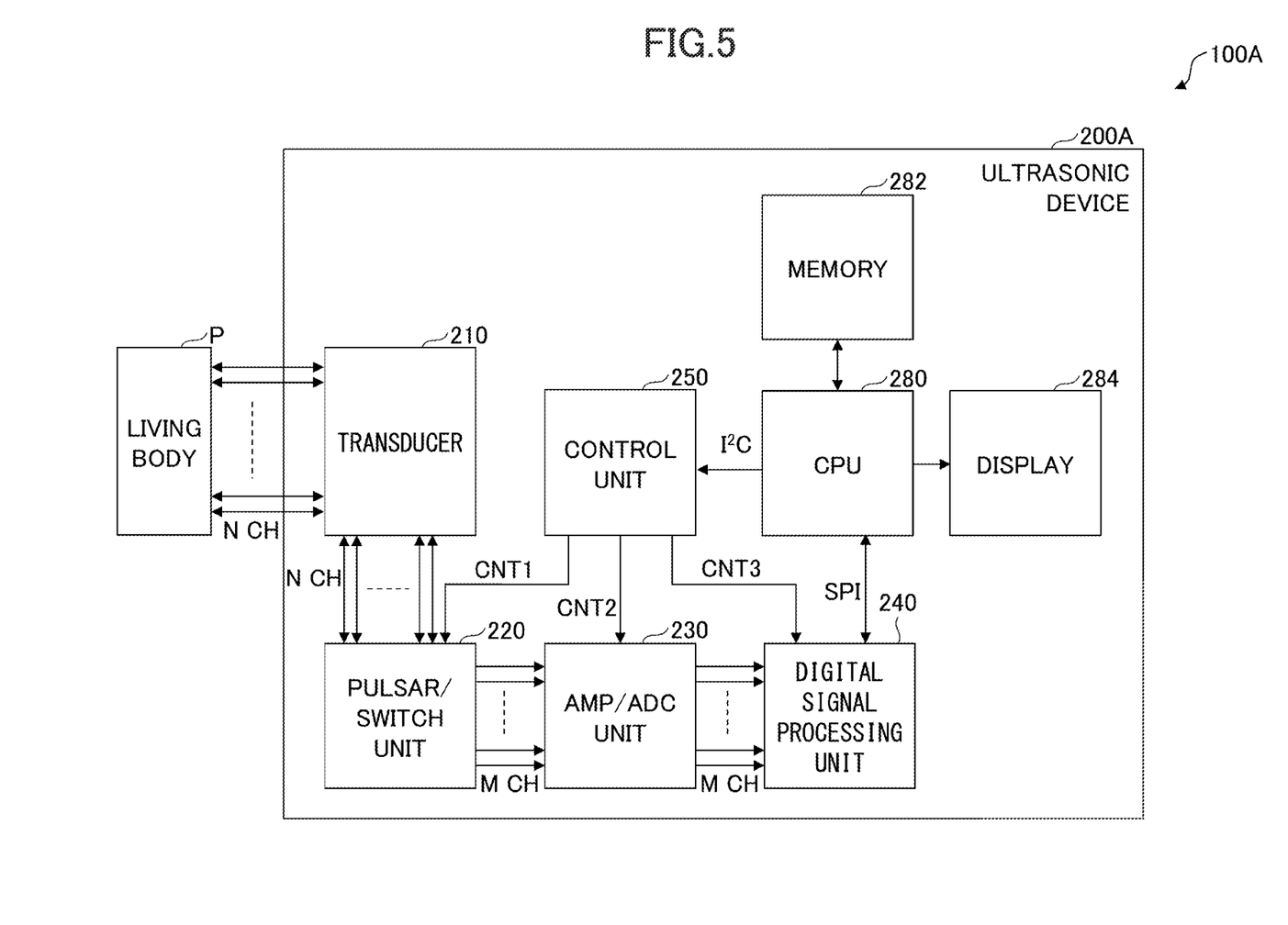
FIG. 5 is a block diagram illustrating an example of an ultrasonic diagnostic system including an ultrasonic device in a second embodiment.

FIG. 5 illustrates an example of an ultrasonic diagnostic system 100A including an ultrasonic device 200A in a second embodiment. Elements that are substantially the same as those in FIG. 1 are assigned the same symbol reference numerals, and detailed description is omitted. In this embodiment, the ultrasonic diagnostic system 100A includes only an ultrasonic device 200A. In other words, the ultrasonic device 200A includes the functions of the terminal device 300 in FIG. 1.

The ultrasonic device 200A includes a transducer 210, a pulsar/switch unit 220, an AMP/ADC unit 230, a digital signal processing unit 240, a control unit 250, a CPU 280, a memory 282, and a display 284. The CPU 280, the memory 282, and the display 284 are substantially the same as the CPU 320, the memory 330, and the display 340 of the terminal device 300 in FIG. 1, respectively. For example, the ultrasonic device 200A operates using commercial power supply, and thereby, does not have a battery installed. Note that the display 284 may be connected to the outside of the ultrasonic device 200A.

For example, the probe of ultrasonic device 200A includes only the transducer 210 among the elements illustrated in FIG. 5. Therefore, the probe having the transducer 210 built in is connected to the pulsar/switch unit 220 by a cable including N channels of signal lines. The configuration and functions of the AMP/ADC unit 230 and the digital signal processing unit 240 are substantially the same as those of the AMP/ADC unit 230 and the digital signal processing unit 240 in FIG. 2.

In this embodiment, the CPU 280 is connected to the control unit 250 via an I2C interface bus. Therefore, the CPU 280 outputs a command to start or stop measurement of an ultrasonic image to the control unit 250, without an intervening wireless communication unit. In addition, the CPU 280 is connected to the digital signal processing unit 240 via an SPI bus. Therefore, the CPU 280 receives image data from the digital signal processing unit 240, without an intervening wireless communication unit. The operations of the ultrasonic device 200A are substantially the same as those in FIGS. 3 and 4.

As above, also in this embodiment, substantially the same effect as in the embodiment described above can be obtained. For example, image data of different transmission positions can be generated during a period while the AMP/ADC unit 230 is powered down; therefore, the power consumption of the ultrasonic device 200A can be reduced without degrading the image quality. In addition, by generating multiple sets of image data at different transmission positions during a period while the AMP/ADC unit 230 is powered down, the power consumption of the ultrasonic device 200A can be reduced further without degrading the image quality.

Figure 6:
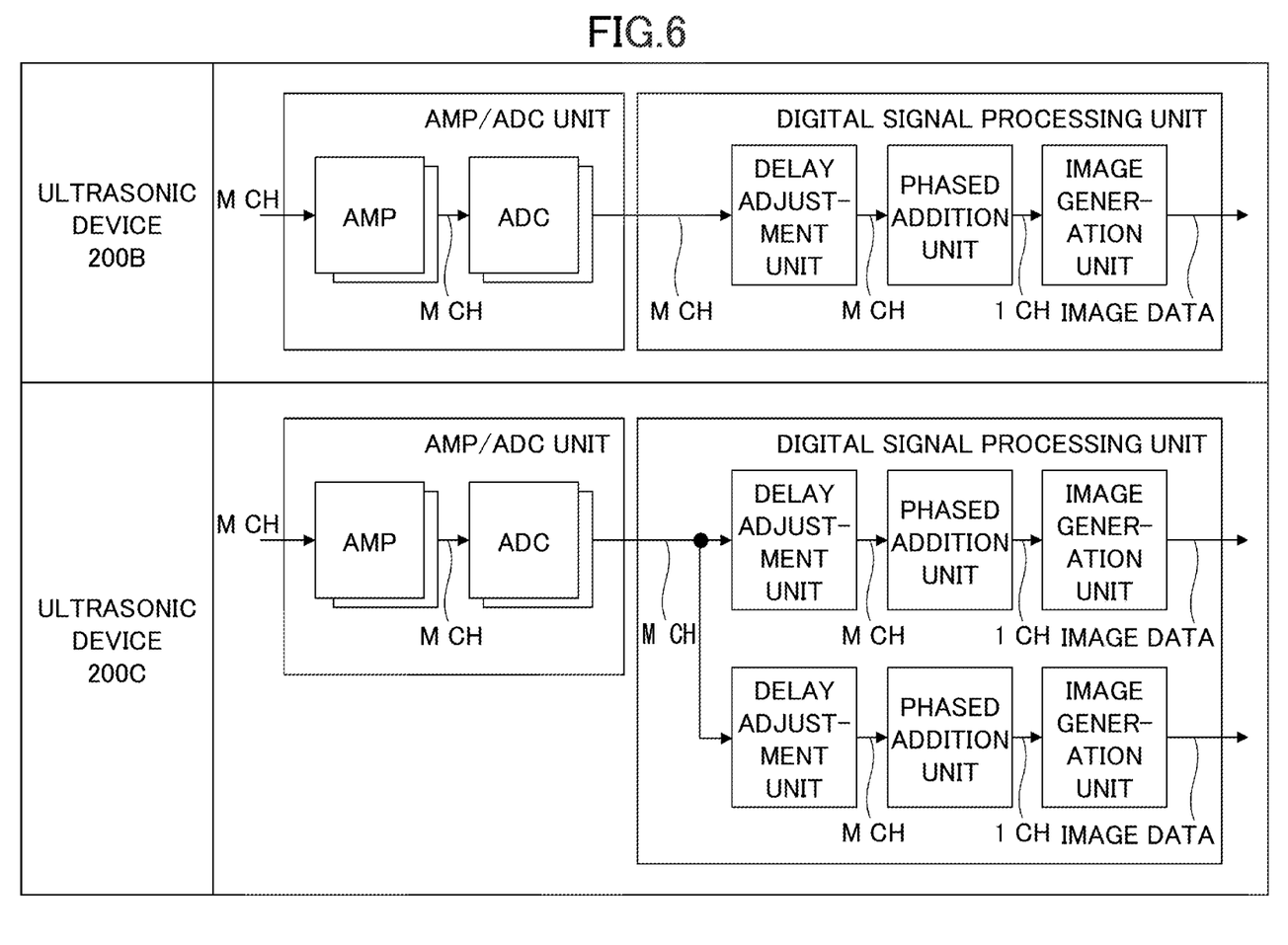
FIG. 6 includes block diagrams illustrating examples (comparative examples) of AMP/ADC units and digital signal processing units of other ultrasonic devices.

FIG. 6 illustrates examples (comparative examples) of AMP/ADC units and digital signal processing units of other ultrasonic devices 200B and 200C. For elements that are substantially the same as in FIG. 2, detailed description is omitted. The AMP/ADC units of the ultrasonic devices 200B and 200C have substantially the same functions as the AMP/ADC unit 230 in FIG. 2, except for operating all the time.

The digital signal processing unit of the ultrasonic device 200B includes a delay adjustment unit, a phased addition unit, and an image generation unit, and does not include units corresponding to the data accumulation unit 241 and the selection unit 242 in FIG. 2. As in the case of the delay adjustment unit 243 in FIG. 2, the delay adjustment unit extracts data with a predetermined amount of delay for each channel from time-series data of M channels output from the ADC, and outputs the extracted data of M channels to the phased addition unit.

As in the case of the phased addition unit 244 in FIG. 2, the phased addition unit adds data of M channels whose amounts of delays are adjusted by the delay adjustment unit, generates one line of data (1 ch) at a transmission position, and outputs the generated one line of data to the image generation unit. As in the case of the image generation unit 245 in FIG. 2, the image generation unit generates the one line of image data at the transmission position based on data received from the phased addition unit. Then, the image data is displayed on a display (not illustrated) as an ultrasonic image.

The digital signal processing unit of the ultrasonic device 200C includes two sets of delay adjustment units, phased addition units, and image generation units. The delay adjustment units operate in parallel and extract data of a predetermined amount of delay for each channel from time-series data of M channels output from the ADC. The data extracted by the two delay adjustment units are data for generating image data of different transmission positions and are different from each other. The phased addition units operate in parallel, and each unit adds data whose amounts of delays have been adjusted from a corresponding one of the delay adjustment units, to generate one line of image data. Then, every time time-series data of M channels is received from the ADC, the ultrasonic device 200C generates two lines of image data.

A method of generating multiple lines of image data in parallel based on time-series data of M channels output from the ADC has been known as a parallel reception method. In a parallel reception method, by having multiple sets of delay adjustment units and phased addition units installed, it becomes possible to generate multiple lines of image data in the time required for generating one line of image data, and thereby, the frame rate can be increased. However, the power consumption becomes greater due to parallel operations, and in the case of applying such a method to an ultrasonic device operated by a battery, the operation time becomes shorter.

Figure 7:
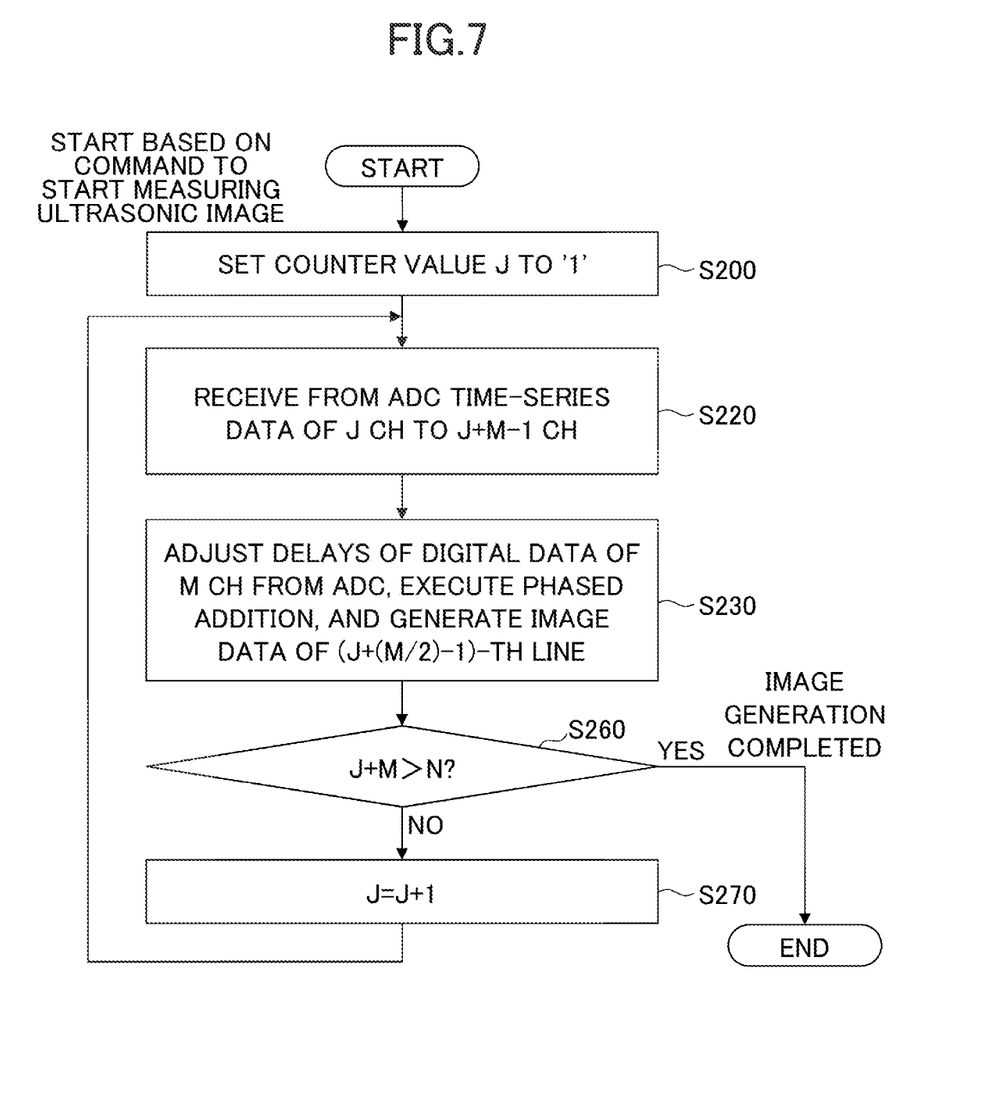
FIG. 7 is a flow chart illustrating an example of operations of an ultrasonic device 200B in FIG. 6.

FIG. 7 illustrates an example of operations of the ultrasonic device 200B in FIG. 6. For operations that are substantially the same as those in FIG. 3, detailed description is omitted. First, at Step S200, the ultrasonic device 200B sets the counter value J to '1'. Next, at Step S220, the digital signal processing unit of the ultrasonic device 200B receives time-series data of M channels from a channel J to a channel J+M−1 output from the AMP/ADC unit. The processing at Step S220 is substantially the same as the processing at Step S120 in FIG. 3, except that time-series data is not accumulated.

Next, at Step S230, as at Step S130 in FIG. 3, by using time-series data from the ADC 232, the digital signal processing unit of the ultrasonic device 200B causes the delay adjustment unit 243 to adjust amounts of delays of the data of M channels. Then, the digital signal processing unit of the ultrasonic device 200B causes the phased addition unit to execute phased addition of the data of M channels whose amounts of delays have been adjusted, to generate image data of the (J+(M/2)−1)-th line.

Next, at Step S260, as at Step S160 in FIG. 3, if the value J+M exceeds the number of channels of the transducer N (the number of oscillation elements), the ultrasonic device 200B completes generation of image data, or if the value J+M is less than or equal to the number of channels N, transitions to Step S270. At Step S270, the ultrasonic device 200B increases the counter value J by '1', and then, returns to the processing at Step S220.

Figure 8:
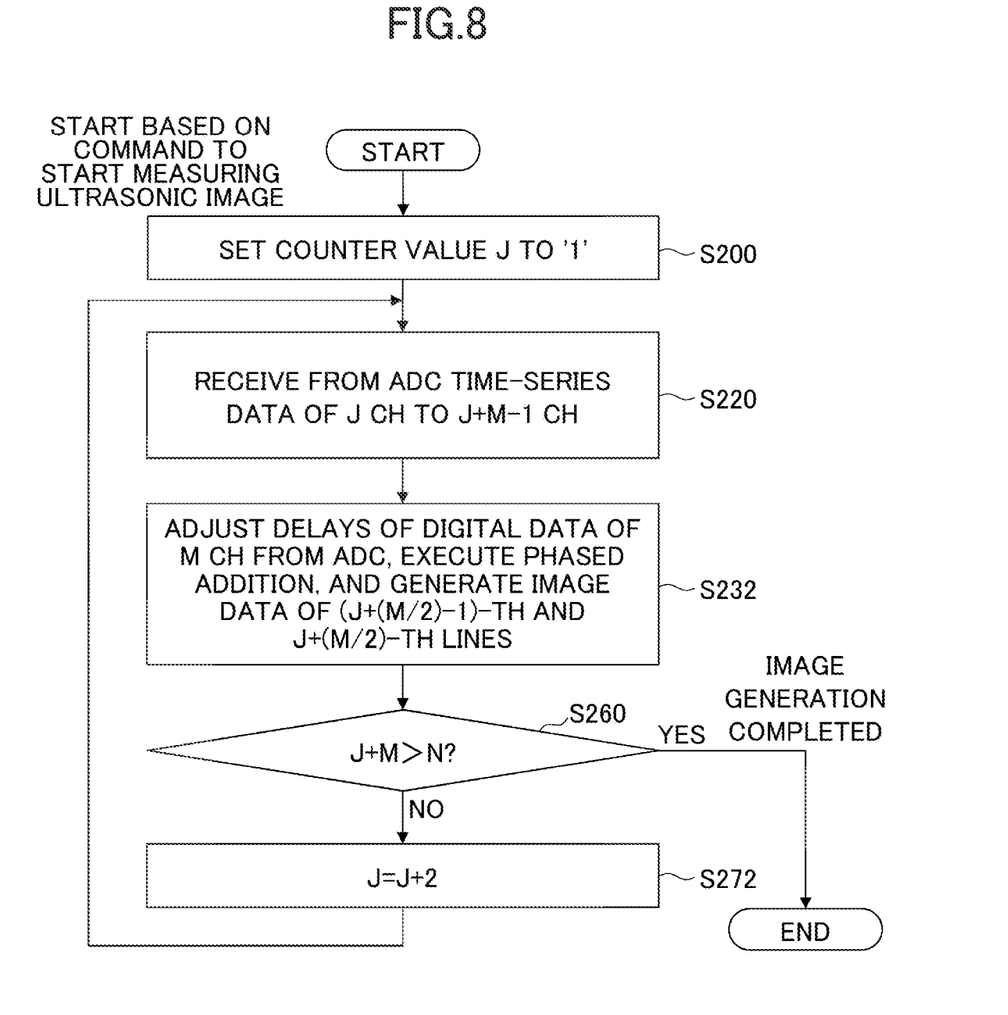
FIG. 8 is a flow chart illustrating an example of operations of an ultrasonic device 200C in FIG. 6.

FIG. 8 illustrates an example of operations of the ultrasonic device 200C in FIG. 6. Operations that are substantially the same as those in FIG. 7 are assigned the same step numbers as in FIG. 7, and detailed description is omitted. FIG. 8 shows substantially the same process as in FIG. 7, except that Step S232 is executed instead of Step S230 in FIG. 7, and Step S272 is executed instead of Step S270 in FIG. 7.

At Step S232, the two delay adjustment units of the ultrasonic device 200C adjust amounts of delays of data corresponding to the (J+(M/2)−1)-th and J+(M/2)-th lines, respectively. The two phased addition units of ultrasonic device 200C execute phased addition of the data of M channels whose amounts of delays have been adjusted and output from the corresponding delay adjustment units, respectively. The two image generation units of ultrasonic device 200C generate image data of the (J+(M/2)−1)-th and (J+(M/2))-th lines, based on the data output from the corresponding phased addition units, respectively.

As above, the present inventive concept has been described based on the respective embodiments; note that the present disclosure is not limited to the requirements set forth in the embodiments described above. These requirements can be changed within a scope not to impair the gist of the present disclosure, and can be suitably defined according to applications.

It should be noted that,
the transducer 210 is an example of a plurality of oscillation elements;
the AMP/ADC unit 230 is an example of a data generator;
the data accumulation unit 241 is an example of a data accumulator;
the selection unit 242 is an example of a selector;
the digital signal processing unit 240 is an example of a data processor;
the delay adjustment unit 243 is an example of a delay adjuster;
the phased addition unit 244 is an example of an adder;
the image generation unit 245 is an example of an image generator;
the control unit 250 is an example of a controller;
the pulsar/switch unit 220 is an example of a switch;
the AMP 231 is an example of an amplifier;
the ADC 232 is an example of an analog-to-digital converter;
the battery 270 is an example of a battery; and the wireless communication unit 260 is an example of a wireless communicator.

What is claimed is:

1. An ultrasonic device comprising:
a plurality of oscillation elements configured to generate ultrasonic waves toward a subject, and generate voltages according to ultrasonic waves reflected by the subject;
a data generator configured to generate a predetermined number of sets of time-series data, each of the sets indicating change in time in a plurality of voltages generated by a predetermined number of oscillation elements, among the voltages generated by the plurality of oscillation elements;
a data accumulator configured to accumulate the sets of time-series data generated by the data generator;
a selector configured to select time-series data from among those generated by the data generator or time-series data from among those accumulated in the data accumulator;
a data processor configured to generate image data by processing a predetermined number of sets of time-series data selected by the selector; and
a controller configured to cause the data generator to stop generating time-series data while the selector selects the time-series data accumulated in the data accumulator such that a power consumption of the ultrasonic device is reduced according to a number of lines of the image data generated using the time-series data.

2. The ultrasonic device as claimed in claim 1, wherein the data processor includes:
a delay adjuster configured to extract sets of data of predetermined amounts of delays from the predetermined number of time-series data selected by the selector;
an adder configured to add the sets of data of the predetermined amounts of delays extracted by the delay adjuster; and
an image generator configured to generate, as the image data, image data at one of a plurality of positions of a measurement region of the subject, based on the data added by the adder.

3. The ultrasonic device as claimed in claim 2, wherein the image generator sequentially generates image data at the plurality of positions of the measurement region of the subject, by using the time-series data accumulated in the data accumulator, and
wherein the delay adjuster changes the data of the predetermined amounts of delays extracted from the predetermined number of time-series data accumulated in the data accumulator, for each of the plurality of positions.

4. The ultrasonic device as claimed in claim 2, further comprising:
a switch configured to select voltages to be generated by the predetermined number of oscillation elements from among the voltages generated by the plurality of oscillation elements,
wherein the controller shifts positions of the predetermined number of oscillation elements selected by the switch by a number of oscillation elements equivalent to a number of items of image data generated by the image generator, every time the data generator generates data.

5. The ultrasonic device as claimed in claim 1, wherein the data generator includes:
a plurality of amplifiers configured to amplify the voltages generated by the predetermined number of oscillation elements, respectively; and
a plurality of analog-to-digital converters configured to sequentially convert values of the plurality of voltages amplified by the plurality of amplifiers into digital data, respectively.

6. The ultrasonic device as claimed in claim 1, further comprising:
a battery configured to supply power to at least the data generator, the data accumulator, the data processor, and the controller.

7. The ultrasonic device as claimed in claim 1, further comprising:
a wireless communicator configured to wirelessly transmit the image data generated by the data processor to a terminal having a display installed to display the image data as an ultrasonic image.

8. A method of controlling an ultrasonic device that includes:
a plurality of oscillation elements configured to generate ultrasonic waves toward a subject, and generate voltages according to ultrasonic waves reflected by the subject; and
a data generator configured to generate a predetermined number of sets of time-series data, each of the sets indicating change in time in a plurality of voltages generated by a predetermined number of oscillation elements, among the voltages generated by the plurality of oscillation elements,
the method comprising:
accumulating the sets of time-series data generated by the data generator in a data accumulator;
selecting time-series data from among those generated by the data generator or time-series data from among those accumulated in the data accumulator;
extracting sets of data of predetermined amounts of delays from a predetermined number of selected time-series data;
adding the sets of extracted data of the predetermined amounts of delays;
generating image data at one of a plurality of positions of a measurement region of the subject, based on the added data; and
causing the data generator to stop generating time-series data while the selector selects the time-series data accumulated in the data accumulator such that a power consumption of the ultrasonic device is reduced according to a number of lines of the image data generated using the time-series data.

* * * * *